United States Patent
Yuguchi et al.

[11] Patent Number: 5,275,787
[45] Date of Patent: Jan. 4, 1994

[54] APPARATUS FOR SEPARATING OR MEASURING PARTICLES TO BE EXAMINED IN A SAMPLE FLUID

[75] Inventors: Naoki Yuguchi, Yokohama; Yoshito Yoneyama; Junichi Yamayoshi, both of Kawasaki, all of Japan

[73] Assignee: Canon Kabushiki Kaisha, Tokyo, Japan

[21] Appl. No.: 928,773

[22] Filed: Aug. 17, 1992

Related U.S. Application Data

[63] Continuation of Ser. No. 588,747, Sep. 27, 1990, abandoned.

[30] Foreign Application Priority Data

Oct. 4, 1989 [JP] Japan .................. 1-260707
Jun. 15, 1990 [JP] Japan .................. 2-157015

[51] Int. Cl.$^5$ ...................... G01N 21/00; G01N 33/48
[52] U.S. Cl. .................................. 422/82.08; 422/68.1; 356/39; 209/579
[58] Field of Search .................. 422/82.08, 73, 68.1; 436/158, 164, 172; 209/3.1, 579, 906; 222/420; 417/207, 208, 209; 356/39

[56] References Cited

U.S. PATENT DOCUMENTS

| | | | |
|---|---|---|---|
| 3,380,584 | 4/1968 | Fulwyler | 209/3 |
| 3,596,275 | 7/1971 | Sweet | 346/75 |
| 3,710,933 | 1/1973 | Fulwyler et al. | 209/3 |
| 3,741,726 | 6/1973 | Mitchell et al. | 436/180 |
| 3,826,364 | 7/1974 | Bonner et al. | 209/3 |
| 4,097,373 | 6/1978 | Allred | 209/111.5 |
| 4,243,318 | 1/1981 | Stöhr | 356/39 |
| 4,318,483 | 3/1982 | Lombardo et al. | 209/3.1 |
| 4,325,483 | 4/1982 | Lombardo et al. | 209/3.1 |
| 4,515,274 | 5/1985 | Hollinger et al. | 209/906 |
| 4,526,276 | 7/1985 | Shoor et al. | 209/552 |
| 4,546,360 | 10/1985 | Fischbeck et al. | 346/1.1 |
| 4,660,971 | 4/1987 | Sage et al. | 356/39 |
| 4,661,913 | 4/1987 | Wu et al. | 422/82.08 |
| 4,662,742 | 5/1987 | Chupp | 356/39 |
| 4,723,129 | 2/1988 | Endo et al. | 346/1.1 |
| 4,740,796 | 4/1988 | Endo et al. | 346/1.1 |
| 4,863,264 | 9/1989 | Miyake et al. | 356/39 |
| 4,934,564 | 6/1990 | Piatt | 222/14 |

FOREIGN PATENT DOCUMENTS

| | | |
|---|---|---|
| 119573 | 9/1984 | European Pat. Off. |
| 268237 | 5/1988 | European Pat. Off. |
| WO8700282 | 1/1987 | PCT Int'l Appl. |

OTHER PUBLICATIONS

Chen et al., "Feedback for Synchronized Pressure Jet Using Optical Sensor", May 1974.
A. Asai, et al., "Bubble Generation Mechanism in the Bubble Jet Recording Process," Journal of Imaging Technology, vol. 14., No. 5, pp. 120-124 Oct. 1988).

Primary Examiner—Robert J. Warden
Assistant Examiner—T. A. Trembley
Attorney, Agent, or Firm—Fitzpatrick, Cella, Harper & Scinto

[57] ABSTRACT

A particle-separating apparatus discharges a liquid drop by providing discharging energy within a receptacle for receiving a particle-suspending fluid. Thermal energy can be used to generate a bubble and discharge a liquid drop containing an individual particle to be examined from an opening in the receptacle.

6 Claims, 10 Drawing Sheets

CELL-SUSPENDING FLUID

APPARATUS FOR SEPARATING OR MEASURING PARTICLES TO BE EXAMINED IN A SAMPLE FLUID

This application is a continuation of application Ser. No. 07/588,747 filed Sep. 27, 1990, now abandoned.

BACKGROUND OF THE INVENTION

1. Field of the Invention

This invention relates to an apparatus and a method for individually separating particles to be examined in a sample fluid in which fine particles, such as cells or the like, are suspended, and also to an apparatus and a method for measuring the separated individual particle by an optical method or the like.

2. Description of the Prior Art

Figure 14:
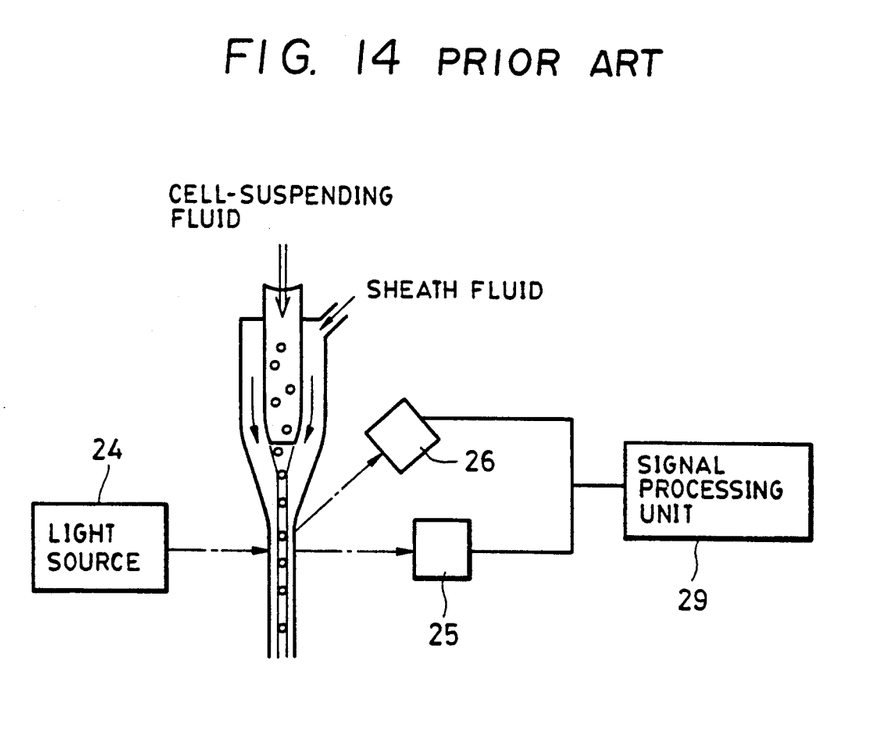
FIG. 14 is a diagram for explaining the sheath flow method.

Heretofore, as a method for individually separating a large number of particles in a particle-suspending fluid, such as a blood sample or the like, a sheath flow method as shown in FIG. 14 has been generally known. In this method, a particle-suspending fluid and a sheath fluid are pressurized by respective pressurizing devices, and the particle-suspending fluid flows in a state surrounded by the sheath liquid. The particle-suspending fluid is hydrodynamically converged into a narrow flow, and the particles are separated and flow one by one in a row.

An apparatus for analyzing or sampling cells, in which a sample, such as blood or the like, is prepared and respective cells in the sample separated by the sheath flow method are measured by an optical method or the like, has been practically utilized in the name of a flow cytometer or a cell sorter.

FIG. 14 shows an example of the configuration of a flow cytometer, which irradiates energy for measurement such as a light beam from a light source 24 onto respective cells separated by the sheath flow method and flowing in a row within a flow cell, and performs photometry of an optical reaction due to the light irradiation onto the cells such as scattered light and fluorescence issued from the cells by detectors 25 and 26. A signal processing unit 29 calculates the kind, size and the like of the analyzed particle according to an output of the photometry.

Figure 15:
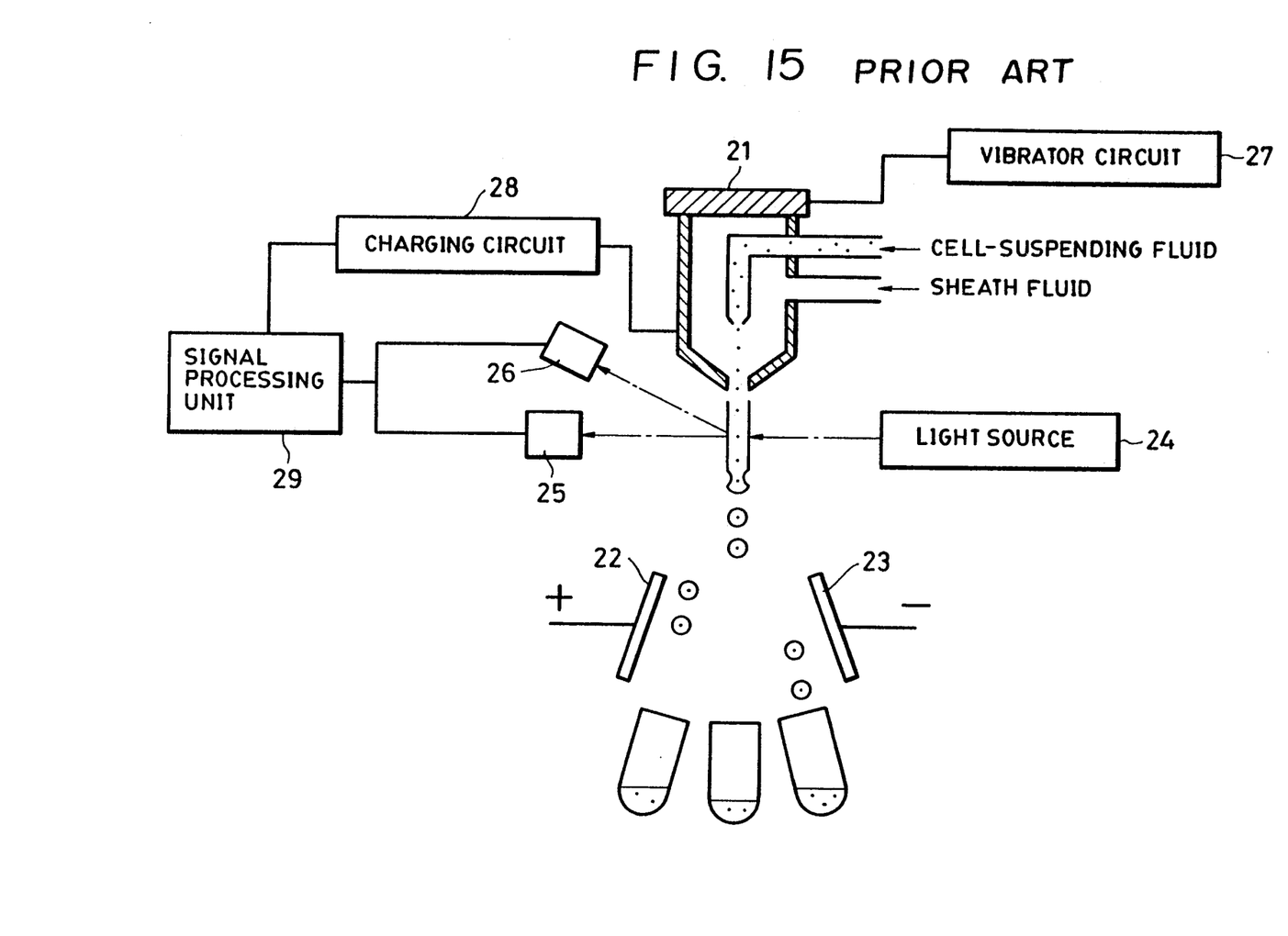
FIG. 15 is a diagram showing the configuration of a conventional example.

The basic principle of the cell sorter has been explained in, for example, U.S. Pat. Nos. 3,380,584, 3,710,933 and 3,826,364. FIG. 15 shows an example of the basic configuration of a cell sorter. A cell-suspending fluid, such as blood or the like, is introduced into a nozzle by an external pressurizing apparatus, and a laminar flow composed substantially of the cell-suspending fluid is produced within the nozzle by the sheath flow principle. A jet stream of the cell-suspending fluid having an average diameter of 15-20 $\mu$m is discharged in the air from an orifice (having a diameter of 70-100 $\mu$m) disposed at the nozzle outlet. Exciting light from a light source 24 is projected onto the jet stream discharged into the air at a position about 100-200 $\mu$m from the front end of the nozzle. When the exciting light is projected onto a cell previously subjected to fluorescent staining, scattered light and fluorescence are issued from the cell, are detected by the detectors 25 and 26, and are converted into electric signals. Since the nozzle is vibrated by a vibrator 21 with a frequency of about 40 kHz (kilohertz) by the control of a vibrator circuit 27, the jet stream discharged from the orifice is converted into uniform liquid drops at a position a few mm lower than the front end of the nozzle. In accordance with whether or not a signal detected from the cell satisfies predetermined conditions, the signal is transmitted from a signal processing unit 29 to a charging circuit 28, from which a charging signal is supplied to the nozzle in synchronization with the liquid-drop formation to slightly charge a liquid drop. While the charged liquid drop containing the desired cell passes between two electrodes 22 and 23 producing a strong electric field, the liquid drop is deflected and distributed in the right or left direction by static electricity in accordance with the kind or the like of the cell, and is collected in one of separate test tubes.

In the sheath flow method utilized in the above-described flow cytometer or cell sorter, since the cell-suspending fluid and the sheath fluid are guided to the nozzle by pressurizing the respective fluids by the pressurizing systems, piping and pressurizing devices, such as pumps or the like, are needed for that purpose. Hence, this method has the disadvantages of needing a large apparatus and complicated control system.

In the sheath flow method, flow rate is determined by pressurizing forces for the cell-suspending fluid and the sheath fluid, and the time interval for the separation of particles is determined by the flow rate and the degree of dilution of the cell-suspending fluid. It is difficult to freely set the time interval, that is, the timing for the separation over a wide range. The method also has the disadvantage that a certain time is needed from the formation of the flow to the start of the separation and from the stoppage of the flow to the stoppage of the separation, and the sample therefore flows uselessly.

Furthermore, it is difficult to provide a small apparatus, and it is also difficult to provide a plurality of apparatuses in parallel in high density to increase processing capability.

SUMMARY OF THE INVENTION

It is an object of the present invention to provide a novel apparatus and method for separating particles, different from the conventional sheath flow method, and an apparatus and a method for measuring particles using the above-described apparatus and method.

It is a further object of the present invention to provide a low-cost and compact apparatus and method.

It is a still further object of the present invention to provide an apparatus and a method capable of separating and measuring particles to be examined without using pressurizing mechanisms.

It is still another object of the present invention to provide an apparatus and a method capable of separating and measuring particles to be examined with a free timing.

It is still a further object of the present invention to provide an apparatus and a method capable of performing the separation of particles to be examined and the start and stoppage of measurement without time lag.

It is still another object of the present invention to provide an apparatus and a method capable of separating and measuring particles to be examined while reducing the amount of wasted sample as much as possible.

It is still another object of the present invention to provide an apparatus and a method having a high processing capability by arranging nozzles in parallel.

In accordance with one aspect of Applicants' invention, an apparatus for separating particles to be examined in a sample fluid comprises a receiving member, having a discharging opening, for receiving the sample fluid, and a thermal energy generation source for generating a bubble in the sample fluid for discharging the sample liquid containing individual particles.

In accordance with another aspect of Applicants' invention, an apparatus for separating particles to be examined in a sample fluid and for measuring each of the separated particles to be examined at a detection portion is provided. The apparatus includes a receiving member, having a discharging opening for receiving the sample liquid, and a thermal energy generation source for generating a bubble in the sample fluid for discharging the liquid containing individual particles. In addition, energy providing means provides the individual particles with energy for measurement, and measuring means measures the individual particles provided with the energy.

DETAILED DESCRIPTION OF THE PREFERRED EMBODIMENTS

Embodiments of the present invention will now be explained in detail with reference to the drawings. FIGS. 1 through 4 are diagrams showing the configuration of a first embodiment of the present invention.

Figure 1:
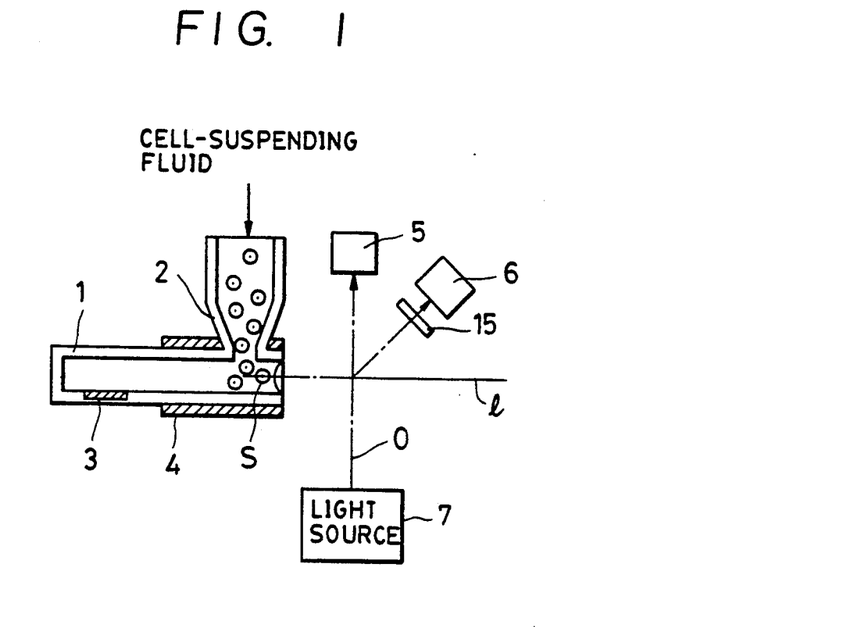
FIGS. 1 through 4 are diagrams showing the configuration of a first embodiment of the present invention.

In FIG. 1, a nozzle 1 includes a receptacle having a rectangular cross section of about 50 $\mu$m × 50 $\mu$m for receiving a cell-suspending fluid in which cells, serving as particles to be examined, are suspended. One end of the nozzle 1 is opened to form an opening. The nozzle is generally produced by a method in which a fine groove is formed on a substrate by etching or a photoresist process and a flat plate is then adhered to the substrate. The production of the nozzle is of course not limited to this method. The cross section of the nozzle may have a size suitable for the size of particles to be examined, serving as an object of measurement. In the present embodiment, blood is selected as an object of measurement. Since the sizes of various blood cells contained within blood are about 5 $\mu$m–30 $\mu$m, the size of the nozzle was set to 50 $\mu$m × 50 $\mu$m, which is a little larger than the maximum size of blood cells.

A supply port 2 for sequentially supplying the cell-suspending fluid into the nozzle 1 is connected to a portion near the exit of the nozzle 1. A heating member 3 is provided within the nozzle, which actually is a heater. The electrode of the heating member 3 is connected to a control circuit (to be described later). The heating member 3 may be situated outside the nozzle and heat the inside of the nozzle. The heating member 3 is not limited to a heater, but may be a means for generating thermal energy which is energy for discharging liquid drops. It may, for example, perform heating by providing a heat-absorbing member with electromagnetic energy, such as laser light or the like. A heat-radiating member 4 provided outside the nozzle 1 prevents the temperature of the nozzle 1 from rising due to thermal conduction from the heater.

A laser light source 7 serves as an energy generation means for measurement. Detectors 5 and 6, such as photomultipliers or the like, detect optical reaction from a particle caused by light irradiation. The laser light source 7 is arranged so that the optical axis O of the laser light emitted from the laser light source 7 crosses the axis l of the path along which the liquid drops discharged from the opening in the nozzle 1 travel. The detector 5 is arranged on the optical axis of the laser light. A condenser lens (not shown) and a beam stopper (not shown) for preventing the laser beam from directly entering the detector 5 are provided in front of the detector 5 on the optical axis to form a dark-field optical system. Thus, only the light scattered in the forward direction of the optical path is detected by the detector 5. The detector 6 is arranged in a direction perpendicular to each of the optical axis O of the laser light and the axis l of the liquid drop discharge. A condenser lens (not shown) and a wavelength selection filter 15 for transmitting only the wavelength of fluorescence are provided in front of the detector 6. Thus, only the fluorescence selected by the wavelength selection filter 15 is subjected to photometry by the detector 6. If light scattered in side directions is needed as a measurement parameter, another detector may also be arranged in a direction deviated from the optical axis O.

The operation in the configuration as described above will now be explained.

A blood sample or the like sufficiently diluted and, if necessary, subjected to staining processing by a fluorescent reagent or the like is prepared. The sample is supplied within the nozzle 1 via the supply port 2 so that the nozzle 1 is filled with the sample, as shown in FIG. 1.

Figure 2:
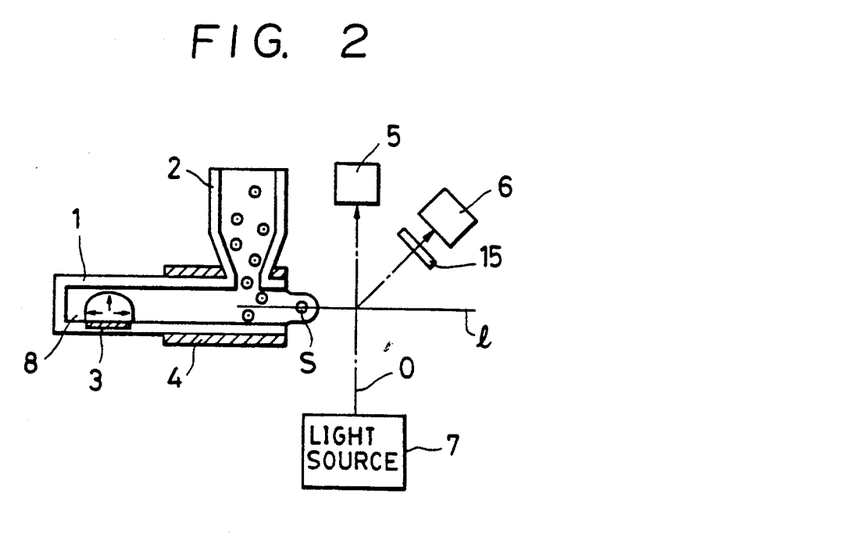
Figure 3:
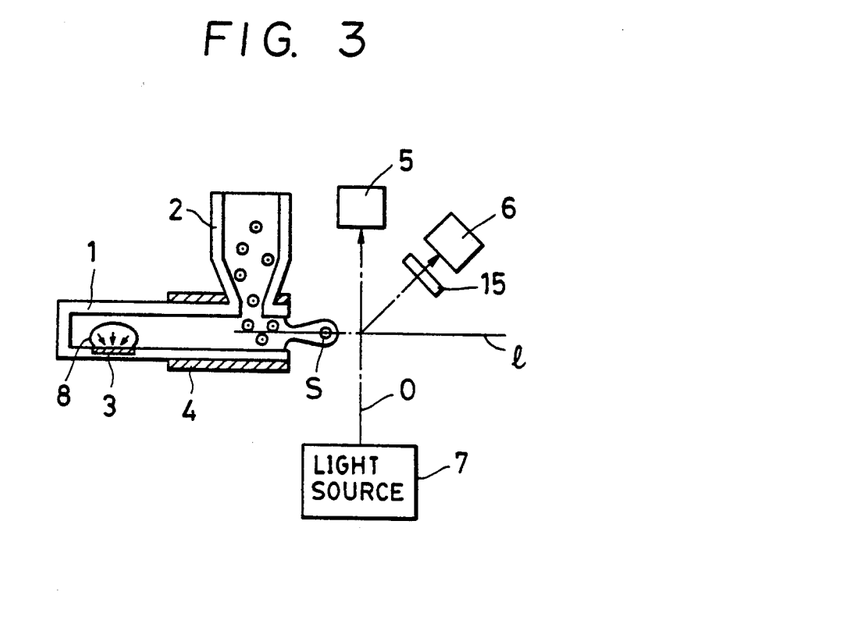
Figure 4:
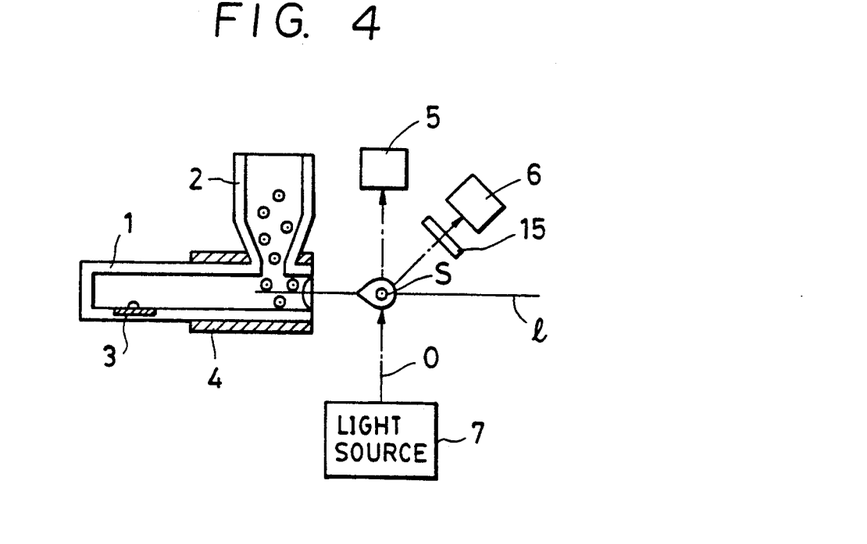
Figure 11:
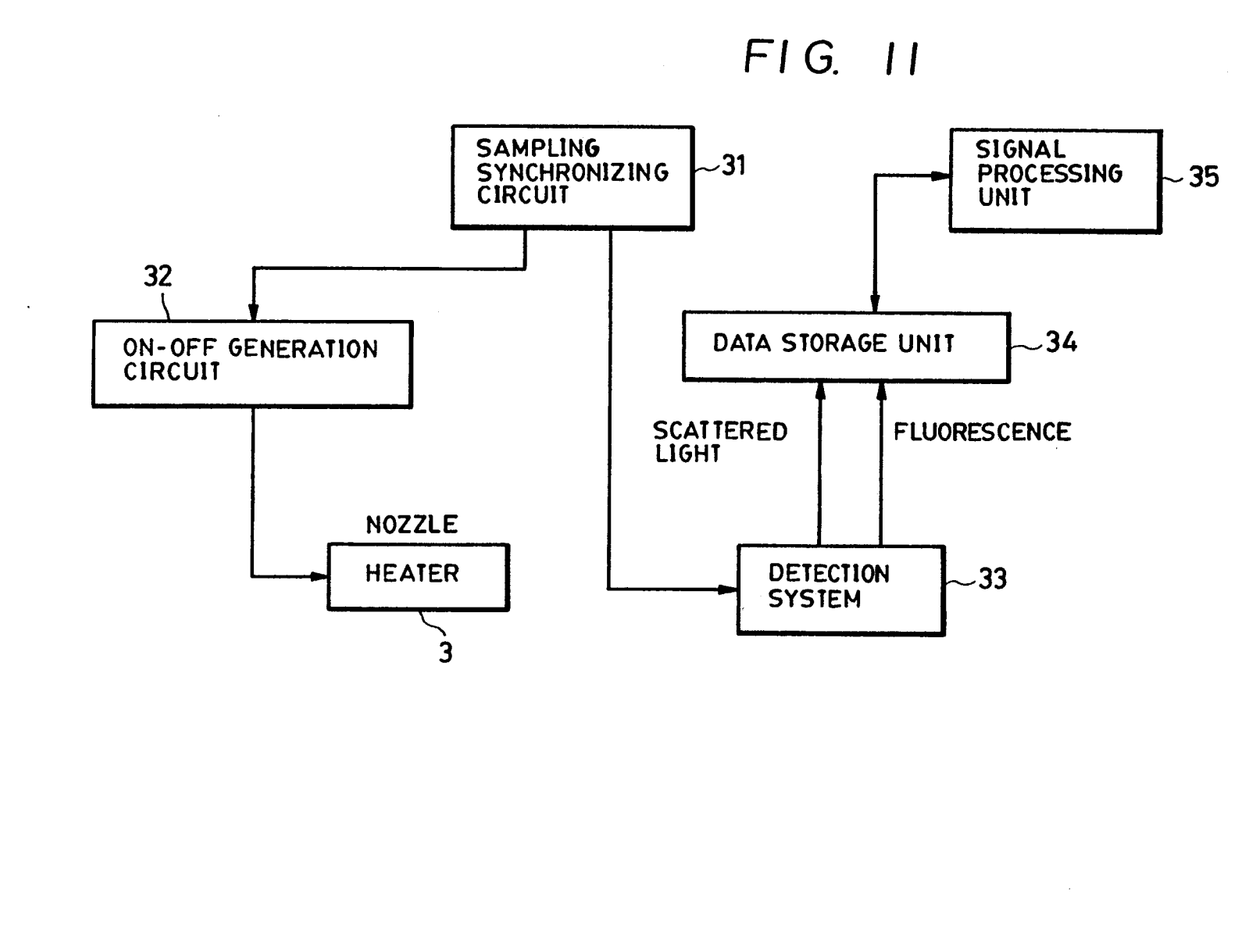
FIG. 11 is a block diagram of a control system.

The control by a control system shown in FIG. 11 will now be explained in detail. Each of the elements shown in block outline of FIG. 11 is well known per se, and its specific type or construction is not critical to carrying out the invention or to a disclosure of the best mode for carrying out the invention. When an on-off generation circuit 32 drives and heats the heater 3 provided within the nozzle 1, water within the cell-suspending fluid is thereby heated instantaneously and vaporizes to generate a bubble 8, as shown in FIG. 2. Since the volume of the fluid abruptly expands by the vaporized amount, a cell S near the opening of the nozzle 1 is extruded outwardly from the opening of the nozzle 1 due to the shock caused by the expansion, and the cell-suspending liquid containing the cell S is discharged outside the nozzle 1, as shown in FIG. 3. The bubble 3 initially continues to expand until it cools and starts to contract, and a drawing force is exerted on the cell-suspending fluid discharged from the opening by the contraction of the volume of the fluid. Thus, the cell-suspending fluid containing the cell S discharged outwardly from the opening is converted into a liquid drop, which flows in the air as shown in FIG. 4. The basic principle of the discharge is described, for example, in U.S. Pat. Nos. 4,723,129 and 4,740,796. The cell-suspending fluid is supplied from the supply port 2 by the discharged amount by capillary forces, and the state shown in FIG. 1 is provided again. Since the supply of the cell-suspending fluid is spontaneously performed by capillary action, a pressurizing mechanism used in the prior art is not needed.

The above-described generation and extinction of the bubble is performed in a very short time in accordance with a sampling frequency provided in a sampling synchronizing circuit 31 shown in FIG. 11. It is possible to continuously discharge several thousands of liquid drops per second at the maximum. It is thereby possible to separate a large number of cells at high speed.

The size of the opening and the capacity of the heater are set so that the liquid drops discharged from the nozzle have diameters of about 50 μm–80 μm. The dilution of the particle-suspending fluid is set so that only a single particle is contained within each of the discharged liquid drops. When each liquid drop crosses a detecting portion onto which energy for measurement, such as a laser beam, is projected, an optical reaction, that is, scattered light and fluorescence due to a cell previously subjected to fluorescent staining contained in the liquid drop, is generated. The optical reaction is detected by a detecting system 33 including detectors 5 and 6. The detecting system 33 receives data from the detectors only during the discharge of the liquid drop in accordance with a timing signal from the sampling synchronizing circuit 31.

Outputs from the detecting system 33 are successively stored in a data storage unit 34. A signal processing unit 35 performs the analysis of particles, such as determining the kind of particles, the properties of particles and the like, from measured data obtained for a large number of particles, using statistical analysis, such as histogram, cytogram and the like. Since various kinds of specific methods of calculation have been widely known, a detailed explanation thereof will be omitted. The results of the analysis are displayed on a CRT monitor, printout from a printer or the like.

In the apparatus of the present invention, timing for separating particles can be freely set over a wide range of time periods. This feature is contrary to the conventional apparatus using the sheath flow method. Hence, it is preferred to set the sampling frequency so that the most suitable speed is provided in consideration of various conditions, such as the required processing speed, the amount of heat generation and durability of the nozzle, and the like. The nozzle is not only continuously driven with a constant frequency, but may also be driven while changing the frequency or with an intermittent frequency. Furthermore, since the inventive apparatus can start and stop without time lag, which is also contrary to the conventional apparatus using the sheath flow method, time and samples are not wasted.

Figure 5:
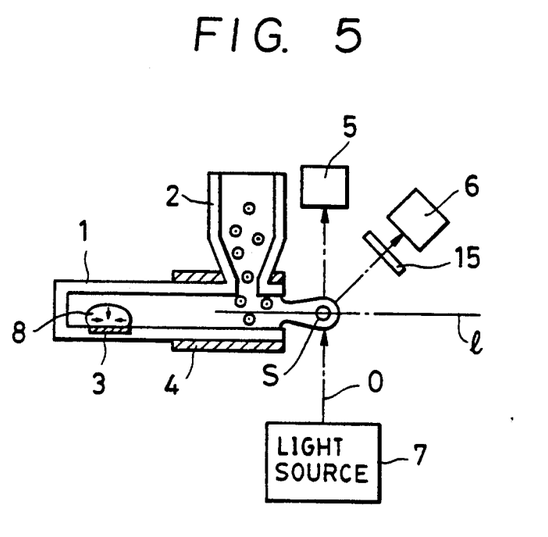
FIG. 5 is a diagram showing the configuration of a second embodiment of the present invention.

FIG. 5 is a diagram showing the configuration of a second embodiment of the present invention. In FIG. 5, components identical or equivalent to those shown in FIG. 1 are indicated by identical numerals.

The present embodiment has a feature in that the detecting portion onto which the laser beam from the light source 7 is projected is situated closer to the opening of the nozzle 1. That is, in the foregoing embodiment, the optical measurement is performed by irradiating the laser light onto a cell in a state in which the cell-suspending fluid is discharged and converted into a liquid drop. In contrast, in the present embodiment the laser light is projected onto a position immediately after the cell-suspending fluid has been discharged and is not yet converted into a liquid drop, as shown in FIG. 5.

Figure 6:
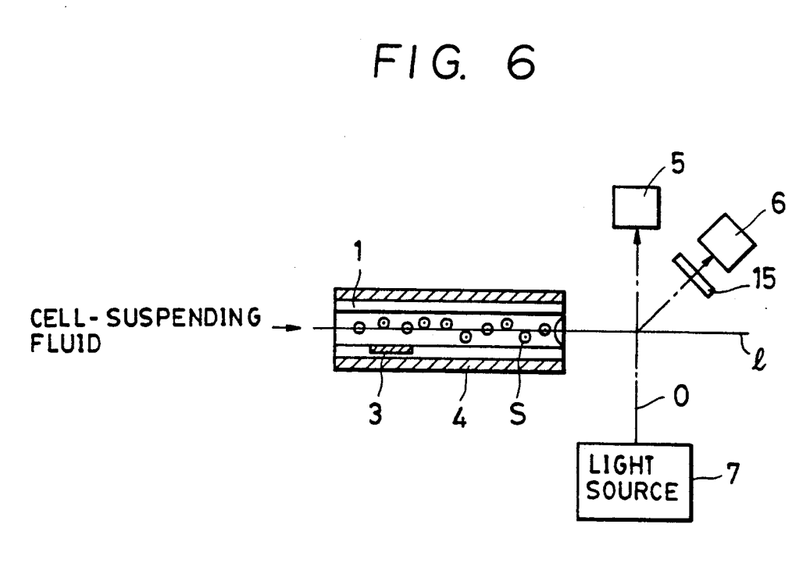
FIGS. 6 and 7 are diagrams showing the configuration of a third embodiment of the present invention.
Figure 7:
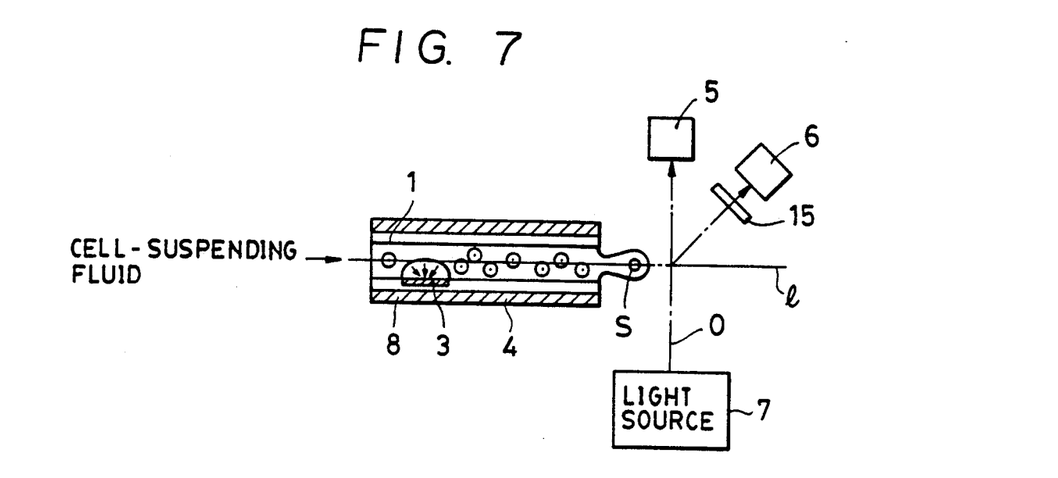

FIGS. 6 and 7 are diagrams showing the configuration of a third embodiment which is more simplified. In these figures, components identical or equivalent to those shown in the foregoing diagrams are indicated by identical numerals.

The cell-suspending fluid is supplied to a nozzle 1 having a supply port at one end and a discharge port at the other port, and each liquid drop containing a cell is discharged from the discharge port of the nozzle due to heating by the heater 3.

Since optical measurement for the discharged liquid drop is identical to that in the first and second embodiments, an explanation thereof will be omitted.

Figure 8:
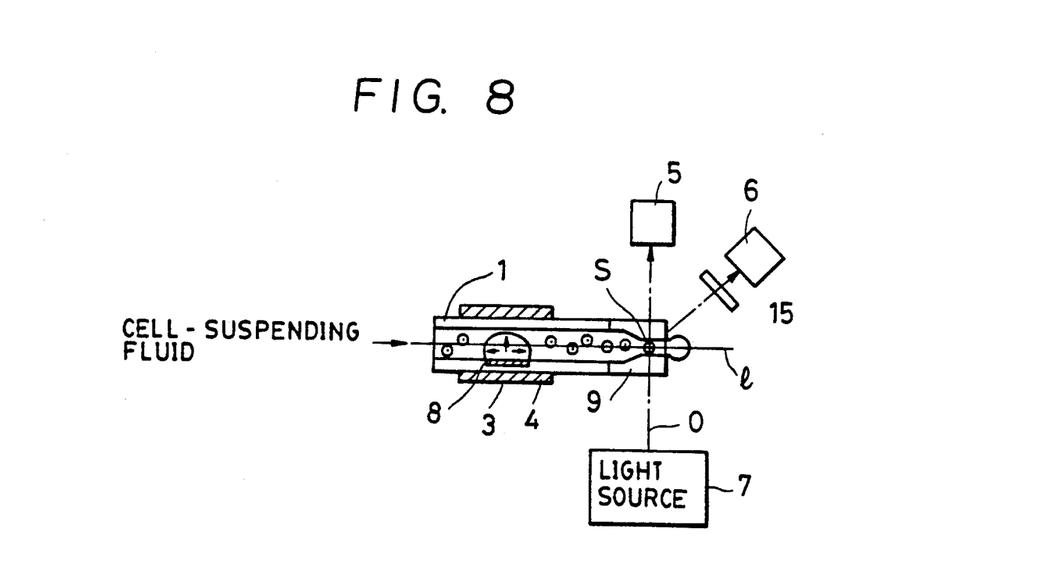
FIG. 8 is a diagram showing the configuration of a fourth embodiment of the present invention.

FIG. 8 is a diagram showing the configuration of a fourth embodiment of the present invention. In FIG. 8, components identical or equivalent to those shown in the foregoing diagrams are indicated by identical numerals.

A nozzle tip 9 made of a transparent material is provided at the front-end portion of the nozzle 1. The path within the nozzle tip 9 is tapered at the side of the nozzle, and has a narrower tube so that sample cells flow one by one in a row.

A light beam is projected onto the nozzle tip 9 from the light source 7, and scattered light and fluorescence from a particle passing a detecting portion within the narrow tube in the nozzle tip 9 onto which the light beam is projected are subjected to photometry by the detectors 5 and 6.

When a bubble 8 is generated due to heating by the heater 3, the cell-suspending fluid within the nozzle 1 is pressed by an expanded volume. The sample cells thereby pass one by one through the narrow tube portion in the cell 9 and are discharged from the opening.

Although one or more cells may successively pass the detecting portion in the nozzle tip 9 by a single heating operation, it is possible to perform photometry for each of the cells as long as the cells flow one by one in a row.

In the present embodiment, optical measurement is not performed when the cell is discharged in the air, but is performed by irradiating light in a state in which the sample cell flows within the transparent cell. Hence, the optical measurement is not influenced by variations in the refractive index of the suspending fluid surrounding the cell and diffused reflection at the surface of liquid drop, and it is always possible to obtain a stable measured value.

Next, a fifth embodiment of the present invention will be explained by reference to FIGS. 9 and 10. In these figures, components identical or equivalent to those shown in the foregoing embodiments are indicated by identical numerals.

Figure 9:
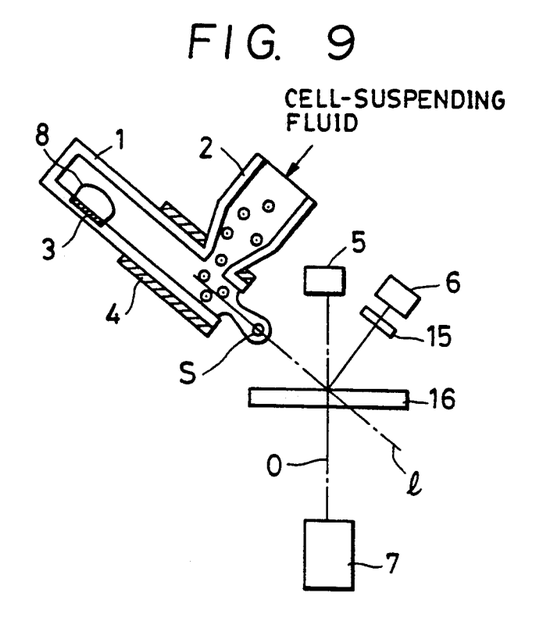
FIGS. 9 and 10 are diagrams showing the configuration of a fifth embodiment of the present invention.
Figure 10:
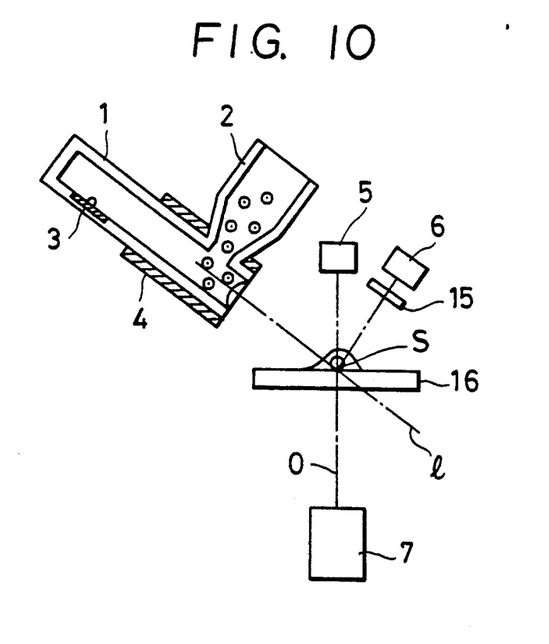

In FIGS. 9 and 10, a fixed transparent glass plate 16 is arranged tilted relative to the discharge axis l of the nozzle 1. The laser beam emitted from the laser light source 7 is incident from the back of the glass plate 16. The discharge axis l of the nozzle 1 and the optical axis O of the laser light are arranged so as to cross near the glass plate 16. The detector 5 is arranged on the optical axis of the laser light. A condenser lens (not shown) and a beam stopper (not shown) for preventing the laser beam from directly entering the detector 5 are provided in front of the detector 5 on the optical axis. The condenser lens and beam stopper form a dark-field optical system so that light scattered in forward directions of the optical axis by a particle S situated at a measuring position on the glass plate 16 onto which the laser beam is projected is subjected to photometry by the detector 5. The detector 6 is arranged in a direction crossing each of the optical axis O of the laser light and the axis 1 of the liquid drop discharge. A condenser lens (not shown) and the wavelength selection filter 15 are provided in front of the detector 6 so that fluorescence emitted from the particle S at the measuring position is selectively subjected to photometry by the detector 6.

Liquid drops discharged from the opening collide with the glass plate 16 from an oblique direction, adhere on the glass plate 16, and move on the glass plate 16 due to the energy of the discharge. When a cell in the fluid passes the measuring position onto which the laser beam is projected from the back of the glass plate 16, scattered light and fluorescence are generated from the cell, the intensities of which are detected by the detecting system consisting of the detectors 5 and 6. The liquid drops are successively discharged from the opening of the nozzle 1, and each cell is measured at the measuring position. The measured cells are pushed away by the subsequently discharged liquid drops.

Since the present embodiment does not have the configuration in which the laser beam is directly projected onto flying liquid drops, but performs measurement by sequentially passing cell particles through the measuring portion while making them adhere to the fixed glass plate, the following effects can be obtained.

First, since the cell particles adhere on the fixed glass plate, measurement can always be performed at a fixed position. Accordingly, there is little deviation in the position of the particle at the detecting position, and so a more stable measurement can be performed.

Second, in a configuration in which the laser beam is directly projected onto a flying liquid drop, diffused reflection occurs at the surface of the liquid drop having an unstable shape of the surface, which may adversely influence the value of photometry for the cell particle in the liquid drop. To the contrary, since the present embodiment has the configuration in which the laser beam is projected from the back of the transparent glass plate and a cell particle in the liquid adhering to the glass plate is measured, no diffused reflection occurs. Accordingly, it is possible to perform measurement which substantially is as reliable as when particles in a flow cell are measured.

Figure 12:
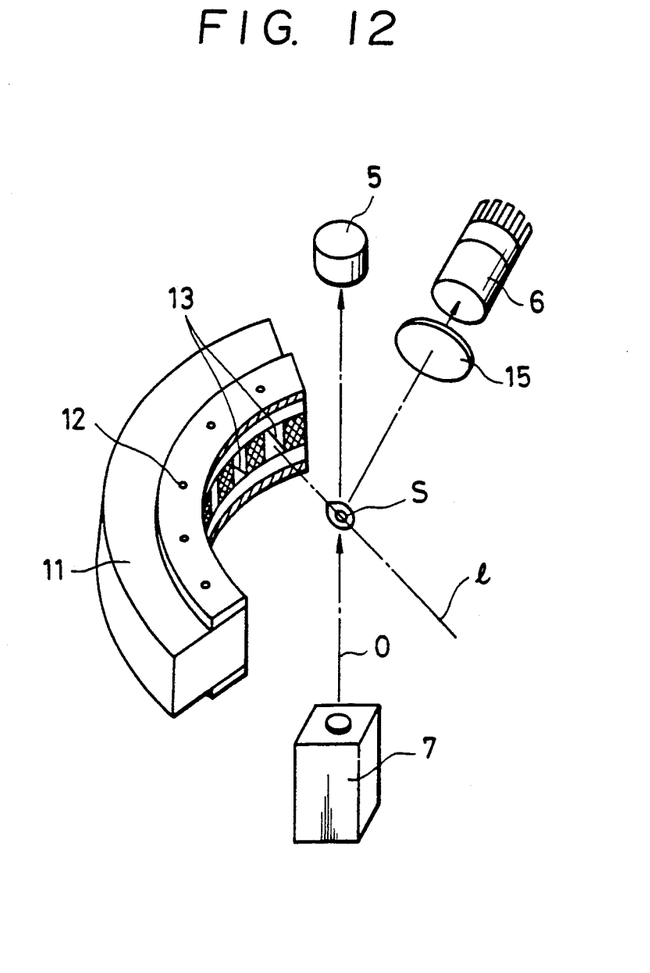
FIG. 12 is a diagram showing the configuration of a sixth embodiment of the present invention.

FIG. 12 is a diagram showing the configuration of a sixth embodiment of the present invention. Since a nozzle for receiving the cell-suspending fluid and for discharging liquid drops has a very small cross section and a structure which can be made by simple processes, such as etching and the like, a plurality of nozzles can easily be provided in parallel in high density.

In FIG. 12, a plurality of nozzles are radially arranged around a predetermined detecting portion on the optical axis of the laser light. In FIG. 12, a nozzle unit 11 comprises a plurality of (five) nozzles having the structure shown in FIG. 1 arranged in parallel. The number of the nozzles is of course not limited to five. The nozzle unit can be made, for example, by providing a plurality of fine grooves on a substrate by etching and then attaching a flat plate to the substrate.

There is also shown a supply port 12 for the cell-suspending fluid, and an opening 13 of the nozzle unit 11. Each nozzle may also have a structure as shown in FIG. 6.

Since each nozzle is nearly radially arranged around the detecting portion onto which the laser beam is projected, liquid drops sequentially discharged from the respective nozzles necessarily pass an identical detecting portion. Thus, only a single optical system for measurement is needed. If a glass plate is disposed at the detecting portion and measurement is performed after liquid drops have adhered thereto, as shown in the fifth embodiment, reliability in measurement is further improved.

Figure 13:
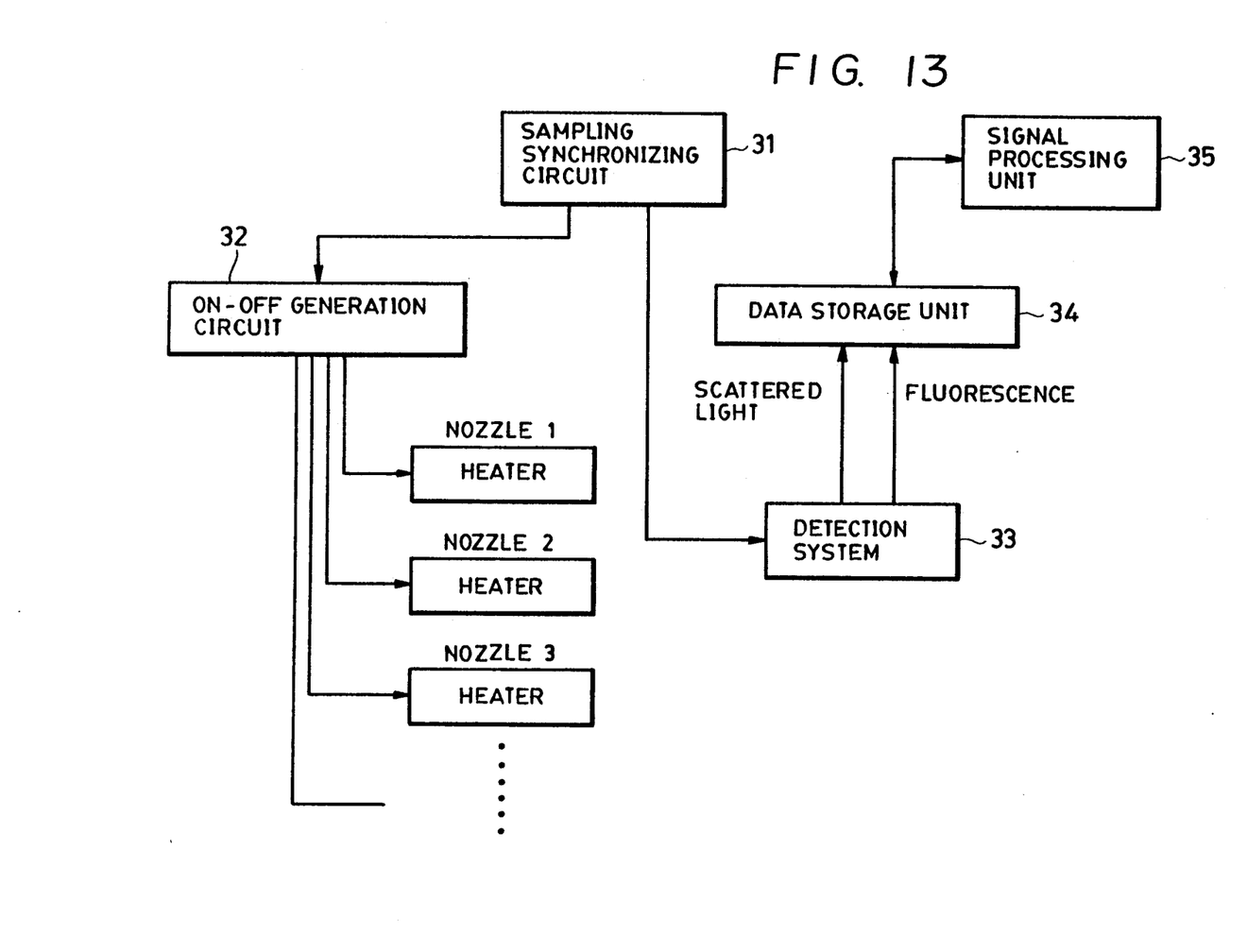
FIG. 13 is a block diagram of a control system used in the sixth embodiment.

Heaters disposed within the nozzle units thus configured are sequentially and time serially driven by a control system shown in FIG. 13, and liquid drops are sequentially discharged from the openings of the respective nozzles. The control system shown in FIG. 13 is identical to the control system shown in FIG. 11 except the number of the nozzles. In FIG. 13, the on-off generation circuit 32 time serially drives the heater of each nozzle in accordance with the sampling frequency generated by the sampling synchronizing circuit 31. The sampling frequency may be a few times the limit frequency in the foregoing embodiments using a single nozzle. This is because the plurality of nozzles are time serially driven and so the period for driving each nozzle becomes a few times smaller than the period when a single nozzle is driven. It is thereby possible to greatly increase measuring speed.

When the temperature of the measuring cells rises, the driving load for each nozzle is reduced and the amount of heat generation is therefore reduced by setting the sampling frequency rather low or by increasing the number of nozzles. Thus, it is possible to reduce adverse influence on the cells due to temperature rise of the nozzles. Increasing the heat capacity of heat-radiating members is also effective for suppressing the temperature rise.

Output signals of scattered light and fluorescence subjected to photometry by the detecting system 33 are detected in accordance with gate signals from the sampling synchronizing circuit 31, and are separately stored in the data storage unit for each liquid drop discharged from each nozzle. That is, even if the kinds of cell-suspending fluids supplied to the respective nozzles are different from one another, measured data are stored discriminating each kind in a single measuring operation. The same kind of objects to be examined may of course be measured in parallel.

According to the present embodiment, since a large number of nozzles are sequentially and time serially driven to successively discharge particles, it is possible to greatly increase processing capability.

Furthermore, since the nozzles are time serially driven, the driving load for each nozzle can be reduced. It is thereby possible to suppress temperature rise of the nozzles, and to increase durability of the nozzles.

Moreover, since the nozzles can be provided in parallel in a very high density, a compact apparatus can be provided. In addition, since only a single photometric system is needed irrespective of the number of the nozzles, the present embodiment is advantageous also from the viewpoint of cost and space.

Although all the above-described embodiments are applied to a so-called flow cytometer for analyzing particles performing photometry, the present invention may also be applied to a cell sorter by providing a sorting mechanism as shown in FIG. 15. In this case, since the cell-suspending fluid can be converted into liquid drops without using a vibrator or pressurizing devices, it is possible to provide a very compact and inexpensive apparatus.

Furthermore, the present invention may also be applied to every kind of apparatus handling sample fluids in which particles to be examined are suspended, such as an apparatus for measuring fine dust particles, an apparatus for measuring industrial fine particles, or the like, in addition to the apparatuses for analyzing fine particles in the biological field, such as blood cells and the like, as shown in the above-described embodiments.

In the above-described embodiments, methods are shown wherein, in order to discharge each liquid drop containing each particle to be examined, a bubble is generated due to thermal energy and a liquid drop is discharged due to the shock produced by the expansion of the bubble. However, another method may also be used in which a liquid drop is discharged due to a shock produced by a mechanical change in volume using a vibrator, such as a piezoelectric element or the like. Also in this case, it is possible to perform so-called on-demand-type discharge control which discharges a fluid in accordance with an arbitrary discharge timing signal, as in the above-described embodiments utilizing a bubble.

Although the above-described embodiments show the most basic type of optical system for measuring particles, various improved types may be considered in order to perform a more accurate measurement. If, for example, the irradiating optical system is provided in the form of a scanning optical system to perform high-speed optical scanning of the measuring portion, it is possible to further increase tolerance for the position deviation of particles to be examined. An acousto-optical deflector (AOD), a rotating mirror, a vibrating mirror and the like are generally used as means for scanning. If an array sensor, such as a coupled device (CCD) or the like, is used as the photosensor, it is possible to catch image information of particles to be examined, and therefore to increase the amount of analyzing information.

The measurement of each particle at the detecting portion where energy for measurement is provided is not limited to the optical method as described above, but various methods of measurement are possible, such as electrical measurement using electric impedance, measurement using electromagnetic energy, a photo-acoustic method and the like.

What is claimed is:

1. A sample inspection system, comprising:
   receptacle means for containing only sample fluid with suspended particles, said receptacle means having an opening;
   a thermal energy generation source disposed within said receptacle means for providing the sample fluid in said receptacle means with a pulse energy to discharge a droplet of the sample fluid from the opening, each droplet containing a particle;
   a detector for detecting the particle; and
   a synchronizing circuit for synchronizing the discharge by said energy generator and the detection by said detector.

2. A sample inspection system, comprising:
   receptacle means for receiving only a sample fluid with suspended particles, said receptacle means having an opening;
   a thermal energy generation source disposed within said receptacle means for providing the sample fluid in said receptacle means with a pulse energy to discharge a droplet of the sample fluid from the opening, each droplet containing a particle;
   a transparent plate facing the opening, the sample fluid discharged from the opening being received on said transparent plate; and
   a detector for detecting the particle on said transparent plate.

3. A sample inspection system, comprising:
   receptacle means for receiving only sample fluid with suspended particles, said receptacle means having an opening;
   a thermal energy generation source disposed within said receptacle means for providing the sample fluid in said receptacle means with a pulse energy to discharge a droplet of the sample fluid from the opening, each droplet containing one particle;
   a detector for detecting the particle;
   a data storage memory for storing data detected by said detector; and
   a signal processor for analyzing the data stored in said data storage memory.

4. A system according to one of claims 1 to 3, wherein said thermal energy generation source includes a heater.

5. A system according to one of claims 1 to 3, further comprising a light source for irradiating the particle with light, wherein said detector detects scattered light or fluorescent light.

6. A system according to one of claims 1 to 3, further comprising a plurality of said receptacle means and said thermal energy generation source, with each of said receptacle means provided with one of said thermal energy generation sources.

* * * * *

UNITED STATES PATENT AND TRADEMARK OFFICE
CERTIFICATE OF CORRECTION

PATENT NO. : 5,275,787
DATED : January 4, 1994
INVENTOR(S) : Yuguchi et al.

It is certified that error appears in the above-indentified patent and that said Letters Patent is hereby corrected as shown below:

COLUMN 9:

Line 37, "coupled" should read --charge-coupled--.

COLUMN 10:

Line 49, "source," should read --sources,--.

Signed and Sealed this

Twenty-fifth Day of October, 1994

Attest:

BRUCE LEHMAN

Attesting Officer

Commissioner of Patents and Trademarks